US012606811B2

(12) United States Patent
Degering et al.

(10) Patent No.: US 12,606,811 B2
(45) **Date of Patent: \*Apr. 21, 2026**

(54) CLEANING PERFORMANCE ON PROTEIN SENSITIVE SOILINGS VI

(71) Applicant: Henkel AG & Co. KGaA, Duesseldorf (DE)

(72) Inventors: Christian Degering, Erkrath (DE); Susanne Wieland, Zons/Dormagen (DE); Fabian Falkenberg, Juechen (DE); Nina Mussmann, Willich (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 1190 days.

This patent is subject to a terminal disclaimer.

(21) Appl. No.: 17/607,037

(22) PCT Filed: Apr. 14, 2020

(86) PCT No.: PCT/EP2020/060375
§ 371 (c)(1),
(2) Date: Oct. 28, 2021

(87) PCT Pub. No.: WO2020/221578
PCT Pub. Date: Nov. 5, 2020

(65) Prior Publication Data
US 2022/0064621 A1      Mar. 3, 2022

(30) Foreign Application Priority Data
Apr. 29, 2019    (DE) ..................... 10 2019 111 075.0

(51) Int. Cl.
*C12N 9/54*        (2006.01)
*C11D 3/386*      (2006.01)
(52) U.S. Cl.
CPC ................ *C12N 9/54* (2013.01); *C11D 3/386* (2013.01); *C12Y 304/21062* (2013.01)
(58) Field of Classification Search
CPC .... C12N 9/54; C11D 3/386; C12Y 304/21062
See application file for complete search history.

(56) References Cited

U.S. PATENT DOCUMENTS

| | | | | |
|---|---|---|---|---|
| 10,767,142 | B2 * | 9/2020 | Mussmann ............ | C11D 3/386 |
| 11,124,742 | B2 | 9/2021 | Mussmann et al. | |
| 2009/0170745 | A1 | 7/2009 | Merkel et al. | |
| 2019/0112552 | A1 | 4/2019 | Mussmann et al. | |
| 2021/0163912 | A1 | 6/2021 | Mussmann et al. | |

FOREIGN PATENT DOCUMENTS

| | | | |
|---|---|---|---|
| DE | 102016204814 A1 | 9/2017 | |
| DE | 102016204815 A1 * | 9/2017 | ............. C11D 3/386 |
| DE | 102016208463 A1 | 11/2017 | |
| DE | 102017215628 A1 | 3/2019 | |
| DE | 102017215629 A1 | 3/2019 | |
| EP | 2016175 | 11/2007 | |
| WO | 2009121725 A1 | 10/2009 | |
| WO | 2017198488 A1 | 11/2017 | |
| WO | WO-2019048495 A1 * | 3/2019 | .............. C12N 9/54 |

OTHER PUBLICATIONS

Mussmann et al. Search results filed on Feb. 6, 2025, 20250206_153759_us-17-607-037-1subt3ap9xn130xt133xn144xn252xq271x.minpct70_dx.rag, Result 3.*
Richard Bott et al. "Subtilisin Enzymes: Practical Protein Engineering", 1996, pp. 75-93, Plenum Press, New York and London.
Stephen F. Altschul et al., "Basic Local Alignment Search Tool", J. Mol. Biol., 1990, pp. 403-410, vol. 215, Academic Press Limited.
Stephen F. Altschul et al., "Gapped BLAST and PSI-BLAST: a new generation of protein database search programs", Nucleic Acids Research, 1997, pp. 3389-3402, vol. 25, No. 17.
Ramu Chenna et al. "Multiple sequence alignment with the Clustal series of programs", Nucleic Acids Research, 2003, pp. 3497-3500, vol. 31, No. 13, Oxford University Press.
Cédric Notredame et al., "T-Coffee: A Novel Method for Fast and Accurate Multiple Sequence Alignment", J. Mol. Biol., 2000, pp. 205-217, vol. 302, Academic Press.
E. G. Delmar et al., "A Sensitive New Substrate for Chymotrypsin", Analytical Biochemistry, 1979, pp. 316-320, vol. 99, Academic Press, Inc.
Allan G. Gornall et al., "Determination of Serum Proteins By Means of the Biuret Reaction", J. Biol. Chem., 1948, pp. 751-766, vol. 177.
Myron L. Bender et al., "The Determination of the Concentration of Hydrolytic Enzyme Solutions : a-Chymotrypsin, Trypsin, Papain, Elastase, Subtilisin, and Acetylcholinesterase", Journal of the American Chemical Society, 1966, pp. 5890-5913.
J. Sambrock et al., "Molecular Cloning, A Laboratory Manual", 1989, Second Edition, Cold Spring Harbor Laboratory Press, 30 pages.
International Search Report from parallel PCT-application PCT/EP2020/060375 dated Sep. 1, 2020, 9 pages, for information purpose only.

(Continued)

*Primary Examiner* — Lynn Y Fan

(74) *Attorney, Agent, or Firm* — CANTOR COLBURN LLP

(57) ABSTRACT

Proteases may include an amino acid sequence having at least 70% sequence identity with the amino acid sequence given in SEQ ID NO:1 over its entire length and, in each case based on the numbering according to SEQ ID NO:1. The protease may have (i) amino acid substitutions, such as 9T, 133A, 144K, 252T and 271E, at the positions corresponding to positions 9, 133, 144, 252 and 271; and (ii) at least one further amino acid substitution at at least one of the positions corresponding to positions 3, 4, 82, 156, 162 or 218. The production and use of said proteases help to improve cleaning performance.

11 Claims, No Drawings

Specification includes a Sequence Listing.

(56)                References Cited

OTHER PUBLICATIONS

Philip N. Bryan "Protein engineering of subtilisin", Biochimica et
Biophysica Acta 1543, 2000, pp. 203-222, Elsevier.
Written Opinion for International Appl. No. PCT/EP2020/060375;
International Filing Date: Apr. 14, 2020; Mailing Date: Sep. 1, 2020;
8 pages.

* cited by examiner

CLEANING PERFORMANCE ON PROTEIN SENSITIVE SOILINGS VI

REFERENCE TO A SEQUENCE LISTING SUBMITTED VIA EFS-WEB

The content of the ASCII text file of the sequence listing named "P80345-Sequence_listing_ST25", which is 3 kb in size was created on Apr. 29, 2019 and electronically submitted via EFS-Web herewith; the sequence listing is incorporated by reference in its entirety.

CROSS-REFERENCE TO RELATED APPLICATIONS

The present application is a national stage entry according to 35 U.S.C. § 371 of PCT Application No. PCT/EP2020/060375 filed on Apr. 14, 2020; which claims priority to German Patent Application Serial No. 10 2019 111 075.0 filed on Apr. 29, 2019; all of which are incorporated herein by reference in their entirety and for all purposes.

TECHNICAL FIELD

The disclosure is in the field of enzyme technology and further relates to proteases from *Bacillus pumilus*, the amino acid sequences of which have been altered to give them a better cleaning performance, in particular with regard to use in washing and cleaning agents, and also relates to the nucleic acids coding for said proteases and to the production thereof. The disclosure further relates to the uses of these proteases and to methods in which they are used, as well as to agents containing them, in particular washing and cleaning agents.

BACKGROUND

Proteases are some of the most technically important enzymes. They are the longest established enzymes for washing and cleaning agents, and are contained in virtually all modern, effective washing and cleaning agents. They bring about the decomposition of protein-containing soilings on the item to be cleaned. Of these, in turn, proteases of the subtilisin type (subtilases, subtilopeptidases, EC 3.4.21.62) are particularly important, which are serine proteases due to the catalytically active amino acids. They act as non-specific endopeptidases and hydrolyze any acid amide bonds that are inside peptides or proteins. Their optimum pH is usually in the distinctly alkaline range. An overview of this family is given, for example, in the article "Subtilases: Subtilisin-like Proteases" by R. Siezen, pages 75-95 in "Subtilisin enzymes," published by R. Bott and C. Betzel, New York, 1996. Subtilases are, naturally, formed from microorganisms. In particular, the subtilisins formed and secreted by *Bacillus* species are the most significant group of subtilases.

Examples of the subtilisin proteases preferably used in washing and cleaning agents are the subtilisins BPN' and Carlsberg, the protease PB92, the subtilisins 147 and 309, the protease from *Bacillus lentus*, in particular from *Bacillus lentus* DSM 5483, subtilisin DY and the enzymes thermitase, proteinase K and the proteases TW3 and TW7, which can be classified as subtilases but no longer as subtilisins in the narrower sense, and variants of said proteases having an amino acid sequence that has been altered with respect to the starting protease. Proteases are altered, selectively or randomly, by methods known from the prior art, and are thereby optimized for use in washing and cleaning agents, for example. These methods include point, deletion or insertion mutagenesis, or fusion with other proteins or protein parts. Appropriately optimized variants are therefore known for the majority of proteases known from the prior art.

European patent application EP 2016175 A1 discloses, for example, a protease from *Bacillus pumilus* intended for washing and cleaning agents. In general, only selected proteases are suitable for use in liquid, surfactant-containing preparations in any case. Many proteases do not exhibit sufficient catalytic performance in such preparations. For the use of proteases in cleaning agents, therefore, a high catalytic activity under conditions as they are during a wash cycle and a high storage stability are particularly desirable. Consequently, protease and surfactant-containing liquid formulations from the prior art are disadvantageous in that the proteases contained, under standard washing conditions (e.g. in a temperature range of from 20° C. to 40° C.), do not have satisfactory proteolytic activity or are not storage-stable and the formulations therefore do not exhibit optimal cleaning performance on protease-sensitive soilings.

SUMMARY

Surprisingly, it has now been found that a protease from *Bacillus pumilus* or a sufficiently similar protease (based on the sequence identity), which, based on the numbering according to SEQ ID NO:1, has the amino acid substitutions selected from 9T, 133A, 144K, 252T and 271E at the positions corresponding to positions 9, 133, 144, 252 and 271, and at least one further amino acid substitution at at least one of the positions corresponding to positions 3, 4, 82, 156, 162 and 218, is improved in terms of cleaning performance on protein-sensitive soilings compared to the wild-type form and/or the reference mutant and is therefore particularly suitable for use in washing or cleaning agents.

A protease may include an amino acid sequence which has at least 70% sequence identity with the amino acid sequence given in SEQ ID NO:1 over its entire length and, in each case based on the numbering according to SEQ ID NO:1, has:

(i) amino acid substitutions, preferably selected from the amino acid substitutions 9T, 133A, 144K, 252T and 271E, at the positions corresponding to positions 9, 133, 144, 252 and 271;
  and
  (ii) at least one further amino acid substitution at at least one of the positions corresponding to positions 3, 4, 82, 156, 162 or 218.

In a second aspect, the protease may include an amino acid sequence which has at least 70% sequence identity with the amino acid sequence given in SEQ ID NO:1 over its entire length and, in each case based on the numbering according to SEQ ID NO:1, has (A) at least one amino acid substitution, preferably selected from 3K, 3A, 3R, 3S, 4A, 4I, 4T and 218S, at at least one of the positions corresponding to positions 3, 4 and 218, and/or
  (B) at least one amino acid substitution selected from 156D and 162I at at least one of the positions corresponding to positions 156 and 162.

A method for producing a protease as defined above, may include the substitution of amino acids in a starting protease which has at least 70% sequence identity with the amino acid sequence given in SEQ ID NO:1 over its entire length (i) at the positions corresponding to positions 9, 133, 144, 252 and 271 in SEQ ID NO:1, such that the protease comprises amino acid substitutions, in particular the amino acid substitutions selected from 9T, 133A, 144K, 252T and 271E, at the positions; and (ii) has at least one further amino acid substitution at at least one of the positions corresponding to positions 3, 4, 82, 156, 162 or 218. The protease that can be obtained by this method has at least 70% sequence identity with the amino acid sequence given in SEQ ID NO: 1 over its entire length.

A protease within the meaning of the present patent application therefore covers both the protease as such and a protease produced by a method. All statements regarding the protease therefore relate both to the protease as such and to the proteases produced by means of corresponding methods.

Further aspects relate to the nucleic acids coding for these proteases, to non-human host cells containing proteases or nucleic acids, and to agents comprising proteases, in particular washing and cleaning agents, to washing and cleaning methods, and to uses of the proteases in washing or cleaning agents in order to remove protein-containing soilings.

DETAILED DESCRIPTION

"At least one," as used herein, means one or more, i.e. 1, 2, 3, 4, 5, 6, 7, 8, 9, 10, 11, 12, 13, 14 or more.

The present disclosure is based on the surprising finding by the inventors that amino acid substitutions at the positions described herein result in an improved cleaning performance of this altered protease in washing and cleaning agents.

In various embodiments, a protease is characterized in that it comprises an amino acid sequence which has at least 70% sequence identity with the amino acid sequence given in SEQ ID NO:1 over its entire length and, in each case based on the numbering according to SEQ ID NO:1, has:

(i) amino acid substitutions, preferably selected from the amino acid substitutions 9T, 133A, 144K, 252T and 271E, at the positions corresponding to positions 9, 133, 144, 252 and 271; and (ii) at least one further amino acid substitution at at least one of the positions corresponding to positions 3, 4, 82, 156, 162 and 218.

In various further embodiments, a protease as described herein additionally has an additional amino acid substitution at the position corresponding to position 130. In various embodiments, this additional amino acid substitution is 130D.

In various other embodiments, a protease is characterized in that it comprises an amino acid sequence which has at least 70% sequence identity with the amino acid sequence given in SEQ ID NO:1 over its entire length and, in each case based on the numbering according to SEQ ID NO:1, has (A) at least one amino acid substitution, preferably selected from 3K, 3A, 3R, 3S, 4A, 4I, 4T and 218S, at at least one of the positions corresponding to positions 3, 4 and 218, and/or (B) at least one amino acid substitution selected from 156D and 162I at at least one of the positions corresponding to positions 156 and 162.

In various embodiments, the protease therefore has amino acid substitutions, preferably selected from 9T, 133A, 144K, 252T and 271E, at the positions corresponding to positions 9, 133, 144, 252 and 271, and additionally has at least one, i.e. for example 1, 2, 3, 4, 5 or 6, amino acid substitution(s) at the positions corresponding to positions 3, 4, 9, 82, 156, 162 and 218, which amino acid substitutions are selected from: 3K, 3A, 3R, 3S, 4A, 4I, 4T, 9T, 82F, 156D and 162I and 218S.

In various other embodiments, a protease is characterized in that a) the amino acid substitution at the position corresponding to position 3 is selected from 3K, 3A, 3R and 3S; and/or b) the amino acid substitution at the position corresponding to position 4 is selected from 4A, 4I and 4T; or c) the amino acid substitution at the position corresponding to position 82 is selected from 82F; or d) the amino acid substitution at the position corresponding to position 156 is selected from 156D; and/or e) the amino acid substitution at the position corresponding to position 162 is selected from 162I; or f) the amino acid substitution at the position corresponding to position 218 is selected from 218S.

In further embodiments, a protease is characterized in that a) the amino acid substitution at the position corresponding to position 3 is selected from 3K, 3A and 3S; and/or b) the amino acid substitution at the position corresponding to position 4 is selected from 4A, 4I and 4T; or c) the amino acid substitution at the position corresponding to position 3 is selected from 3R.

In further embodiments, a protease is characterized in that the amino acid substitution at the position corresponding to position 3 is selected from 3K and the amino acid substitution at the position corresponding to position 4 is selected from 4I. In various embodiments, the protease has substitutions at positions 3 and 4, said substitutions preferably being selected from those mentioned herein, preferably (i) 3K and 4I, (ii) 3A and 4I or (iii) 3A and 4A.

In various embodiments, the protease has amino acid substitutions, in particular the amino acid substitutions selected from 9T, 133A, 144K, 252T and 271E, at the positions corresponding to positions 9, 133, 144, 252 and 271; and has at least one, for example 1, 2, 3, 4, 5 or 6, for example 1, 2 or 3, further amino acid substitution(s) at one or more of the positions corresponding to positions 3, 4, 82, 156, 162 or 218, said amino acid substitution(s) preferably being selected from: 3K, 3A, 3R, 3S, 4A, 4I, 4T, 82F, 156D, 162I and 218S. Furthermore, in various further embodiments, a protease additionally has an additional amino acid substitution at the position corresponding to position 130, said amino acid substitution preferably being 130D. Such proteases are disclosed for example as mutants 2-10 in the examples.

The proteases have an improved cleaning performance. In a wide variety of embodiments, the proteases may have a proteolytic activity which, based on the wild type (SEQ ID NO:1), is at least 101%, preferably at least 102% or more. Such performance-enhanced proteases allow improved washing results on proteolytically sensitive soilings in various temperature ranges, in particular in a temperature range of from 20° C. to 40° C.

Independently of or in addition to increased cleaning performance, the proteases may have an increased storage stability in washing or cleaning agents. This means that they may have an increased stability in washing or cleaning agents in comparison with the reference enzyme (according to SEQ ID NO:1), in particular compared to the starting variant of the protease (mutant in the examples), in particular when stored for 3 or more days, 4 or more days, 7 or more days, 10 or more days, 12 or more days, 14 or more days, 21 or more days or 28 or more days.

The proteases exhibit enzymatic activity, i.e. they are capable of hydrolyzing peptides and proteins, in particular in a washing or cleaning agent. A protease n is therefore an enzyme that catalyzes the hydrolysis of amide/peptide bonds in protein/peptide substrates and is thus able to cleave proteins or peptides. Furthermore, a protease is preferably a mature protease, i.e. the catalytically active molecule without signal peptide(s) and/or propeptide(s). Unless stated otherwise, the sequences given also each refer to mature (processed) enzymes.

In various embodiments, the protease is a free enzyme. This means that the protease can act directly with all the components of an agent and, if the agent is a liquid agent, that the protease is in direct contact with the solvent of the agent (e.g. water). In other embodiments, an agent may contain proteases that form an interaction complex with other molecules or which contain a "coating." In this case, an individual protease molecule or a plurality of protease molecules may be separated from the other constituents of the agent by a surrounding structure. Such a separating structure may arise from, but is not limited to, vesicles such as a micelle or a liposome. The surrounding structure may also be a virus particle, a bacterial cell or a eukaryotic cell. In various embodiments, an agent may include cells of *Bacillus pumilus* or *Bacillus subtilis* which express the proteases, or cell culture supernatants of such cells.

In various embodiments, the protease comprises an amino acid sequence which, over its entire length, is preferably at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5% and 98.8% identical to the amino acid sequence given in SEQ ID NO:1, and in each case based on the numbering according to SEQ ID NO: 1, has the amino acid substitutions given above. The protease having the given substitutions means that it contains one (of the given) substitution(s) at the relevant position, i.e. at least the given positions are not otherwise mutated or deleted, for example by fragmentation of the protease.

The identity of nucleic acid or amino acid sequences is determined by a sequence comparison. This sequence comparison is based on the BLAST algorithm established and commonly used in the prior art (see, for example, Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs;" Nucleic Acids Res., 25, p. 3389-3402) and occurs in principle by similar sequences of nucleotides or amino acids in the nucleic acid or amino acid sequences being assigned to one another. The assignment of the relevant positions shown in a table is referred to as an alignment. Another algorithm available in the prior art is the FASTA algorithm. Sequence comparisons (alignments), in particular multiple sequence comparisons, are created using computer programs. The Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on these programs or algorithms are frequently used. Sequence comparisons (alignments) using the computer program Vector NTI® Suite 10.3 (Invitrogen Corporation, 1600 Faraday Avenue, Carlsbad, California, USA) with the predetermined standard parameters, the AlignX module of which program for the sequence comparisons is based on ClustalW, are also possible. Unless stated otherwise, the sequence identity given herein is determined by the BLAST algorithm.

Such a comparison also allows a statement regarding the similarity of the compared sequences. It is usually given in percent identity, i.e. the proportion of identical nucleotides or amino acid residues in said sequences or in an alignment of corresponding positions. The broader concept of homology takes conserved amino acid exchanges into account in the case of amino acid sequences, i.e. amino acids having similar chemical activity, since they usually perform similar chemical activities within the protein. Therefore, the similarity between the compared sequences can also be expressed in percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated.

The indication that an amino acid position corresponds to a numerically designated position in SEQ ID NO: 1 therefore means that the corresponding position is associated with the numerically designated position in SEQ ID NO: 1 in an alignment as defined above.

In a further embodiment, the protease is characterized in that its cleaning performance (after storage, e.g. over 4 weeks) is not significantly reduced compared to that of a protease which is denoted as mutant 1 in the examples and has the correspondingly identified amino acid substitutions, i.e. has at least 80% of the reference washing performance, preferably at least 100%, more preferably at least 110% or more. The cleaning performance can be determined in a washing system containing a washing agent in a dosage between 4.5 and 7.0 grams per liter of washing liquor, and the protease, the proteases to be compared being used in the same concentration (based on active protein), and the cleaning performance on a soiling on cotton being determined by measuring the degree of cleaning of the washed textiles. For example, the washing process can take place for 60 minutes at a temperature of 40° C. and the water can have a water hardness between 15.5 and 16.5° (German hardness). The concentration of the protease in the washing agent intended for this washing system is 0.001 to 0.1 wt. %, preferably 0.01 to 0.06 wt. %, based on active, purified protein.

A liquid reference washing agent for such a washing system may be composed as follows (all figures in wt. %): 4.4% alkyl benzene sulfonic acid, 5.6% further anionic surfactants, 2.4% C12-C18 Na salts of fatty acids (soaps), 4.4% non-ionic surfactants, 0.2% phosphonates, 1.4% citric acid, 0.95% NaOH, 0.01% defoamer, 2% glycerol, 0.08% preservatives, 1% ethanol, and the remainder being demineralized water. Preferably, the dosage of the liquid washing agent is between 4.5 and 6.0 grams per liter of washing liquor, for example 4.7, 4.9 or 5.9 grams per liter of washing liquor. Washing in a pH range between pH 7 and pH 10.5, preferably between pH 7.5 and pH 8.5, is preferred.

The cleaning performance is determined for example at 20° C. or 40° C. using a liquid washing agent as stated above, the washing process preferably being carried out for 60 minutes at 600 rpm.

The degree of whiteness, i.e. the lightening of soilings, as a measure of the cleaning performance is determined by optical measuring methods, preferably photometrically. A suitable device for this purpose is, for example, the Minolta CM508d spectrometer. Usually, the devices used for the measurement are calibrated beforehand with a white standard, preferably a supplied white standard.

The activity-equivalent use of the relevant protease ensures that the respective enzymatic properties, for example the cleaning performance on certain soilings, are compared even if the ratio of active substance to total protein (the values of the specific activity) diverges. In general, a low specific activity can be compensated for by adding a larger amount of protein.

Otherwise, methods for determining protease activity are well known to, and routinely used by, a person skilled in the art of enzyme technology. For example, such methods are disclosed in Tenside, vol. 7 (1970), p. 125-132. Alternatively, the protease activity can be determined by the release of the chromophore para-nitroaniline (pNA) from the substrate suc-L-Ala-L-Ala-L-Pro-L-Phe-p-nitroanilide (AAPF). The protease cleaves the substrate and releases pNA. The release of the pNA causes an increase in absorbance at 410 nm, the temporal progression of which is a measure of the enzymatic activity (cf. Del Mar et al., 1979). The measurement is carried out at a temperature of 25° C., a pH of 8.6, and a wavelength of 410 nm. The measuring time is 5 min and the measuring interval is 20 s to 60 s. The protease activity is usually indicated in protease units (PE). Suitable protease activities are 2.25, 5 or 10 PE per ml of washing liquor, for example. However, the protease activity is not equal to zero.

An alternative test for establishing the proteolytic activity of the proteases is an optical measuring method, preferably a photometric method. The appropriate test involves the protease-dependent cleavage of the substrate protein casein. This is cleaved by the protease into a multitude of smaller partial products. The totality of these partial products has an increased absorption at 290 nm compared with uncleaved casein, it being possible for this increased absorption to be determined using a photometer, and thus for a conclusion to be drawn regarding the enzymatic activity of the protease.

The protein concentration can be determined using known methods, for example the BCA method (bicinchoninic acid; 2,2'-bichinolyl-4,4'-dicarboxylic acid) or the Biuret method. (A. G. Gornall, C. S. Bardawill and M. M. David, J. Biol. Chem., 177 (1948), p. 751-766). The active protein concentration can be determined in this regard by titrating the active centers using a suitable irreversible inhibitor and determining the residual activity (cf. M. Bender et al., J. Am. Chem. Soc. 88, 24 (1966), p. 5890-5913).

In addition to the amino acid alterations discussed above, proteases can have other amino acid alterations, in particular amino acid substitutions, insertions or deletions. Such proteases are, for example, further developed by targeted genetic modification, i.e. by mutagenesis methods, and optimized for specific applications or with regard to specific properties (for example with regard to their catalytic activity, stability, etc.). Furthermore, nucleic acids can be introduced into recombination approaches and can thus be used to generate completely novel proteases or other polypeptides.

The aim is to introduce targeted mutations such as substitutions, insertions or deletions into the known molecules in order, for example, to improve the cleaning performance of enzymes. For this purpose, in particular the surface charges and/or the isoelectric point of the molecules and thus their interactions with the substrate can be altered. For instance, the net charge of the enzymes can be altered in order to influence the substrate binding, in particular for use in washing and cleaning agents. Alternatively or additionally, one or more corresponding mutations can increase the stability or catalytic activity of the protease and thus improve its cleaning performance. Advantageous properties of individual mutations, e.g. individual substitutions, can complement one another. A protease which has already been optimized with regard to specific properties, for example with respect to its stability during storage, can therefore also be further developed.

For the description of substitutions relating to exactly one amino acid position (amino acid exchanges), the following convention is used herein: first, the naturally occurring amino acid is designated in the form of the internationally used one-letter code, followed by the associated sequence position and finally the inserted amino acid. A plurality of exchanges within the same polypeptide chain are separated by slashes. For insertions, additional amino acids are named following the sequence position. In the case of deletions, the missing amino acid is replaced by a symbol, for example a star or a dash, or a Δ is given before the corresponding position. For example, P9T describes the substitution of proline at position 9 by threonine, P9TH describes the insertion of histidine following the amino acid threonine at position 9 and P9* or ΔP9 describes the deletion of proline at position 9. This nomenclature is known to a person skilled in the field of enzyme technology.

The protease may be obtained from a protease as described above as the starting molecule by single or multiple conservative amino acid substitution, the protease in the numbering according to SEQ ID NO: 1 having the above-described amino acid substitutions. The term "conservative amino acid substitution" means the exchange (substitution) of one amino acid residue for another amino acid residue, with this exchange not resulting in a change to the polarity or charge at the position of the exchanged amino acid, e.g. the exchange of a nonpolar amino acid residue for another nonpolar amino acid residue. Conservative amino acid substitutions include, for example: G=A=S, I=V=L=M, D=E, N=Q, K=R, Y=F, S=T, G=A=I=V=L=M=Y=F=W=P=S=T.

Alternatively or in addition, the protease is characterized in that it can be obtained from a protease as the starting molecule by fragmentation or deletion, insertion or substitution mutagenesis and comprises an amino acid sequence which matches the starting molecule over a length of at least 200, 210, 220, 230, 240, 250, 260, 261, 262, 263, 264, 265, 266, 267, 268, 269, 270, 271, 272, 273, or 274 contiguous amino acids, the amino acid substitution(s) described above, i.e. the substitutions 9T, 133A, 144K, 252T and 271E or the substitutions at the positions corresponding to positions 3, 4, 82, 156, 162 and/or 218 and optionally 130, still being present. This means that if the proteases described herein are modified, the modification takes place in such a way that the substitutions are retained.

For instance, it is possible to delete individual amino acids at the termini or in the loops of the enzyme without the proteolytic activity being lost or diminished in the process. Furthermore, such fragmentation or deletion, insertion or substitution mutagenesis can also, for example, reduce the allergenicity of the enzymes concerned and thus improve their overall applicability. Advantageously, the enzymes retain their proteolytic activity even after mutagenesis, i.e. their proteolytic activity corresponds at least to that of the starting enzyme, i.e. in a preferred embodiment the proteolytic activity is at least 80, preferably at least 90%, of the activity of the starting enzyme. Other substitutions can also exhibit advantageous effects. Both single and multiple contiguous amino acids can be exchanged for other amino acids.

The further amino acid positions are in this case defined by an alignment of the amino acid sequence of a protease with the amino acid sequence of the protease from *Bacillus pumilus*, as given in SEQ ID NO:1. Furthermore, the assignment of the positions depends on the mature protein. This assignment is also to be used in particular if the amino acid sequence of a protease comprises a higher number of amino acid residues than the protease from *Bacillus pumilus* according to SEQ ID NO:1. Proceeding from the above-mentioned positions in the amino acid sequence of the protease from *Bacillus pumilus*, the alteration positions in a protease are those which are assigned to precisely these positions in an alignment.

Advantageous positions for sequence alterations, in particular substitutions, of the protease from *Bacillus pumilus*, which are of particular significance when transferred to homologous positions of the proteases and which impart advantageous functional properties to the protease are therefore the positions which correspond to the positions described herein in an alignment, i.e. in the numbering according to SEQ ID NO:1. At the positions mentioned, the following amino acid residues are present in the wild-type molecule of the protease from *Bacillus pumilus*: T3, V4, P9, L82, N130, T133, N144, S156, T162, T218, N252 and Q271.

Further confirmation of the correct assignment of the amino acids to be altered, i.e. in particular their functional correspondence, can be provided by comparative experiments, according to which the two positions assigned to one another on the basis of an alignment are modified in the same way in both compared proteases, and observations are made as to whether the enzymatic activity is modified in the same way in both cases. If, for example, an amino acid exchange in a specific position of the protease from *Bacillus pumilus* according to SEQ ID NO: 1 is accompanied by an alteration of an enzymatic parameter, for example an increase in the KM value, and a corresponding alteration of the enzymatic parameter, for example likewise an increase in the KM value, is observed in a protease variant, of which the amino acid exchange has been achieved by the same introduced amino acid, this can therefore be considered to be confirmation of the correct assignment.

All of these aspects are also applicable to the method for producing a protease. Accordingly, a method further comprises one or more of the following method steps:

a) Introducing a single or multiple conservative amino acid substitution into the protease, the protease comprising amino acid substitutions, preferably the amino acid substitutions selected from 9T, 133A, 144K, 252T and 271E at the positions corresponding to positions 9, 133, 144, 252 and 271; and at least one further amino acid substitution at at least one of the positions corresponding to positions 3, 4, 82, 156, 162 and 218;

b) Altering the amino acid sequence by fragmentation or deletion, insertion or substitution mutagenesis such that the protease comprises an amino acid sequence which matches the starting molecule over a length of at least 200, 210, 220, 230, 240, 250, 260, 261, 262, 263, 264, 265, 266, 267, 268, 269, 270, 271, 272, 273 or 274 contiguous amino acids, the protease comprising the substitutions 9T, 133A, 144K, 252T and 271E at the positions corresponding to positions 9, 133, 144, 252 and 271; and at least one further amino acid substitution at at least one of the positions corresponding to positions 3, 4, 82, 156, 162 and 218.

All embodiments also apply to the method.

In further embodiments, the protease or the protease produced by means of a method is still at least 70%, 71%, 72%, 73%, 74%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 98.8% identical to the amino acid sequence given in SEQ ID NO:1 over its entire length. The protease or the protease produced by means of a method has the amino acid substitutions selected from 9T, 133A, 144K, 252T and 271E at the positions corresponding to positions 9, 133, 144, 252 and 271; and at least one amino acid substitution at at least one of the positions corresponding to positions 3, 4, 82, 156, 162 or 218, in each case based on the numbering according to SEQ ID NO:1.

In various embodiments, proteases according to SEQ ID NO:1 may have the following amino acid substitution variants:

P9T, T133A, N144K, N252T and Q271E combined with
(i) N130D and T218S;
(ii) N130D and L82F;
(iii) N130D, S156D and T162I;
(iv) N130D, T3K and V4I;
(v) N130D, T3A and V4A;
(vi) N130D, T3A and V4I;
(vii) N130D and T3R;
(viii) N130D and V4A;
(ix) N130D, T3S and V4T,
wherein the numbering is in each case based on the numbering according to SEQ ID NO:1. Further examples are the variants described in the examples.

The protease described above may be additionally stabilized, in particular by one or more mutations, for example substitutions, or by coupling to a polymer. An increase in stability during storage and/or during use, for example in the washing process, leads to longer enzymatic activity and thus improves the cleaning performance. In principle, all stabilization options which are described in the prior art and/or are appropriate are considered. Those stabilizations are preferred which are achieved by mutations of the enzyme itself, since such stabilizations do not require any further work steps following the recovery of the enzyme. Examples of sequence alterations suitable for this purpose are mentioned above. Further suitable sequence alterations are known from the prior art.

Further possibilities for stabilization are, for example:

altering the binding of metal ions, in particular the calcium binding sites, for example by exchanging one or more of the amino acid(s) that are involved in the calcium binding with one or more negatively charged amino acids and/or by introducing sequence alterations in at least one of the sequences of the two amino acids arginine and glycine;

protecting against the influence of denaturing agents such as surfactants by mutations that cause an alteration of the amino acid sequence on or at the surface of the protein;

exchanging amino acids near the N-terminus with those likely to contact the rest of the molecule via non-covalent interactions, thus contributing to the maintenance of the globular structure.

Preferred embodiments are those in which the enzyme is stabilized in a plurality of ways, as a plurality of stabilizing mutations act additively or synergistically.

The protease as described above, may have at least one chemical modification. A protease having such an alteration is referred to as a derivative, i.e. the protease is derivatized.

In the context of the present application, derivatives are thus understood to mean those proteins of which the pure amino acid chain has been chemically modified. Such derivatizations can be achieved, for example, in vivo by the host cell that expresses the protein. In this regard, couplings of low-molecular-weight compounds such as lipids or oligosaccharides are particularly noteworthy. However, the derivatizations may also be carried out in vitro, for example by the chemical conversion of a side chain of an amino acid or by covalent bonding of another compound to the protein. For example, it is possible to couple amines to carboxyl groups of an enzyme in order to alter the isoelectric point. Another such compound may also be another protein that is bound to a protein via bifunctional chemical compounds, for example. Derivatization is also understood to mean the covalent bonding to a macromolecular carrier or a non-covalent inclusion in suitable macromolecular cage structures. Derivatizations may, for example, affect the substrate specificity or bonding strength to the substrate or cause a temporary blockage of the enzymatic activity when the coupled substance is an inhibitor. This can be expedient, for example, for the period of storage. Such modifications may further affect the stability or enzymatic activity. They can also be used to reduce the allergenicity and/or immunogenicity of the protein and thus, for example, increase its skin compatibility. For example, couplings with macromolecular compounds, for example polyethylene glycol, can improve the protein in terms of stability and/or skin compatibility.

Derivatives of a protein can also be understood in the broadest sense to mean preparations of these proteins. Depending on the recovery, processing or preparation, a protein can be combined with various other substances, for example from the culture of the producing microorganisms. A protein may also have been deliberately added to other substances, for example to increase its storage stability. Therefore, all preparations of a protein are also usable herein. This is also irrespective of whether or not it actually exhibits this enzymatic activity in a particular preparation. This is because it may be desired that it has no or only low activity during storage and exhibits its enzymatic function only at the time of use. This can be controlled via appropriate accompanying substances, for example. In particular, the joint preparation of proteases with specific inhibitors is possible in this regard.

A nucleic acid may code for a protease, as well as to a vector containing such a nucleic acid, in particular a cloning vector or an expression vector.

These may be DNA or RNA molecules. They can be present as a single strand, as a single strand that is complementary to this single strand, or as a double strand. In particular in the case of DNA molecules, the sequences of the two complementary strands must be taken into account in all three possible reading frames. Furthermore, it should be noted that different codons, i.e. base triplets, can code for the same amino acids, such that a particular amino acid sequence can be coded by a plurality of different nucleic acids. Due to this degeneracy of the genetic code, all of the nucleic acid sequences which can code any of the proteases described above are usable herein. A person skilled in the art is able to determine these nucleic acid sequences unequivocally since, despite the degeneracy of the genetic code, defined amino acids can be assigned to individual codons. Therefore, a person skilled in the art proceeding from an amino acid sequence can easily determine nucleic acids coding for said amino acid sequence. Furthermore, in the case of nucleic acids, one or more codons may be replaced by synonymous codons. This aspect relates in particular to the heterologous expression of the enzymes. For instance, every organism, for example a host cell of a production strain, has a particular codon usage. Codon usage is understood to mean the translation of the genetic code into amino acids by the relevant organism. Bottlenecks can occur in the protein biosynthesis if the codons on the nucleic acid in the organism are faced with a comparatively small number of loaded tRNA molecules. Although coding for the same amino acid, this results in a codon being translated less efficiently in the organism than a synonymous codon coding for the same amino acid. Due to the presence of a higher number of tRNA molecules for the synonymous codon, it can be translated more efficiently in the organism.

Using methods which are currently generally known, such as chemical synthesis or the polymerase chain reaction (PCR), in conjunction with molecular-biological and/or protein-chemical standard methods, it is possible for a person skilled in the art to produce the corresponding nucleic acids and even complete genes on the basis of known DNA and/or amino acid sequences. Such methods are known, for example, from Sambrook, J., Fritsch, E. F. and Maniatis, T. 2001. Molecular cloning: a laboratory manual, $3^{rd}$ Edition Cold Spring Laboratory Press.

Within the meaning of the present disclosure, vectors are understood to mean elements consisting of nucleic acids, which elements contain a nucleic acid as the characteristic nucleic acid region. They are able to establish these as a stable genetic element in a species or cell line over a plurality of generations or cell divisions. Vectors are special plasmids, i.e. circular genetic elements, in particular when used in bacteria. The nucleic acid may be cloned into a vector. The vectors include, for example, those originating from bacterial plasmids, viruses or bacteriophages, or predominantly synthetic vectors or plasmids with elements of a wide variety of origins. By means of the additional genetic elements present in each case, vectors are able to establish themselves as stable units in the corresponding host cells over a plurality of generations. They may be present as separate units in an extrachromosomal manner or integrated into a chromosome or chromosomal DNA.

Expression vectors comprise nucleic acid sequences which enable them to replicate in the host cells containing them, preferably microorganisms, particularly preferably bacteria, and to express a contained nucleic acid there. The expression is in particular influenced by the promoter(s) that regulate the transcription. In principle, the expression can take place by means of the natural promoter originally located before the nucleic acid to be expressed, but also by means of a promoter of the host cell provided on the expression vector or also by means of a modified or completely different promoter of another organism or another host cell. In the present case, at least one promoter is provided for the expression of a nucleic acid and used for the expression thereof. Furthermore, expression vectors can be regulatable, for example by changing the cultivation conditions or when a specific cell density of the host cells containing them is reached or by addition of specific substances, in particular activators of gene expression. An example of such a substance is the galactose derivative isopropyl-β-D-thiogalactopyranoside (IPTG), which is used as an activator of the bacterial lactose operon (lac operon).

In contrast with expression vectors, the nucleic acid contained is not expressed in cloning vectors.

A non-human host cell which contains a nucleic acid or a vector or which contains a protease, in particular one which secretes the protease into the medium surrounding the host cell. Preferably, a nucleic acid or a vector is transformed into a microorganism, which is then a host cell. Alternatively, individual components, i.e. nucleic acid parts or fragments of a nucleic acid, can be introduced into a host cell such that the resulting host cell contains a nucleic acid or a vector. This procedure is particularly suitable when the host cell already contains one or more constituents of a nucleic acid or a vector and the further constituents are then supplemented accordingly. Methods for transforming cells are established in the prior art and are well known to a person skilled in the art. In principle, all cells, i.e. prokaryotic or eukaryotic cells, are suitable as host cells. Host cells that can be managed in a genetically advantageous manner, for example in terms of the transformation with the nucleic acid or the vector and the stable establishment thereof, are preferred, for example unicellular fungi or bacteria. Furthermore, preferred host cells are characterized by good microbiological and biotechnological manageability. This relates, for example, to easy cultivation, high growth rates, low requirements for fermentation media and good production and secretion rates for foreign proteins. Preferred host cells secrete the (transgenically) expressed protein into the medium surrounding the host cells. Furthermore, the proteases can be modified by the cells producing them after their production, for example by attachment of sugar molecules, formylations, aminations, etc. Such post-translational modifications can functionally influence the protease.

Other preferred embodiments are those host cells of which the activity can be regulated on account of genetic regulatory elements, which are, for example, made available on the vector but may also be present in these cells from the outset. These host cells may be induced to express, for example, by the controlled addition of chemical compounds which are used as activators, by modifying the cultivation conditions, or when a specific cell density is reached. This allows economical production of the proteins. An example of such a compound is IPTG, as described above.

Prokaryotic or bacterial cells are preferred host cells. Bacteria are characterized by short generation times and low demands on cultivation conditions. As a result, cost-effective cultivation methods or production methods can be established. In addition, a person skilled in the art has a wealth of experience in the case of bacteria in fermentation technology. For a specific production, gram-negative or gram-positive bacteria may be suitable for a wide variety of reasons to be determined experimentally in individual cases, such as nutrient sources, product formation rate, time requirement, etc.

In the case of gram-negative bacteria, such as *Escherichia coli*, a large number of proteins are secreted into the periplasmic space, i.e. into the compartment between the two membranes enclosing the cells. This may be advantageous for particular applications. Furthermore, gram-negative bacteria can also be designed such that they eject the expressed proteins not only into the periplasmic space, but into the medium surrounding the bacterium. In contrast, gram-positive bacteria such as bacilli or actinomycetes or other representatives of Actinomycetales have no outer membrane, and therefore secreted proteins are released immediately into the medium surrounding the bacteria, usually the nutrient medium, from which the expressed proteins can be purified. They can be isolated directly from the medium or further processed. In addition, gram-positive bacteria are related or identical to most of the origin organisms for technically significant enzymes and usually even form comparable enzymes, meaning that they have a similar codon usage and the protein synthesis apparatus is naturally aligned accordingly.

Host cells may be altered in terms of their requirements for the culture conditions, may have different or additional selection markers or may express other or additional proteins. In particular, this may also involve those host cells which transgenically express a plurality of proteins or enzymes.

Any microorganisms, in particular all fermentable microorganisms, particularly preferably those of the genus *Bacillus*, and may be used to produce proteins by the use of such microorganisms. Such microorganisms then represent host cells.

In a further embodiment, the host cell is characterized in that it is a bacterium, preferably one selected from the group of the genera of *Escherichia, Klebsiella, Bacillus, Staphylococcus, Corynebacterium, Arthrobacter, Streptomyces, Stenotrophomonas* and *Pseudomonas*, more preferably one selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor* and *Stenotrophomonas maltophilia*.

The host cell may also be a eukaryotic cell, however, which is characterized in that it has a cell nucleus. The host cell may have a cell nucleus. In contrast with prokaryotic cells, eukaryotic cells are capable of post-translationally modifying the protein formed. Examples thereof are fungi such as actinomycetes or yeasts such as *Saccharomyces* or *Kluyveromyces*. This can be particularly advantageous, for example, if the proteins are to undergo specific modifications in connection with their synthesis that make such systems possible. Modifications carried out by eukaryotic systems, in particular in connection with the protein synthesis, include, for example, the binding of low-molecular-weight compounds such as membrane anchors or oligosaccharides. Such oligosaccharide modifications may be desirable, for example, to lower the allergenicity of an expressed protein. Co-expression with the enzymes naturally formed by such cells, such as cellulases, may be advantageous. Furthermore, for example, thermophilic fungal expression systems may be particularly suitable for the expression of temperature-resistant proteins or variants.

The host cells are cultivated and fermented in the conventional way, for example in discontinuous or continuous systems. In the first case, a suitable nutrient medium is inoculated with the host cells and the product is harvested from the medium after a period to be determined experimentally. Continuous fermentations are characterized by the achievement of a flow equilibrium, in which cells partially die over a comparatively long period of time but also grow back and the protein formed can be removed from the medium at the same time.

Host cells are preferably used to produce proteases. A method for producing a protease, may include:

a) cultivating a host cell, and b) isolating the protease from the culture medium or from the host cell.

Fermentation processes are known per se from the prior art and represent the actual large-scale production step, usually followed by a suitable purification method of the prepared product, for example the proteases. All fermentation processes which are based on a corresponding method for producing a protease constitute embodiments usable herein.

Fermentation processes which are characterized in that the fermentation is carried out via a feed strategy shall be considered in particular. In this case, the media constituents that are consumed by the continuous cultivation are added. As a result, considerable increases can be achieved both in the cell density and in the cell mass or dry mass and/or in particular in the activity of the protease of interest. Furthermore, the fermentation can also be designed in such a way that undesired metabolic products are filtered out or neutralized by adding buffers or suitable counter ions.

The produced protease can be harvested from the fermentation medium. Such a fermentation process is preferable to isolation of the protease from the host cell, i.e. product preparation from the cell mass (dry matter), but requires the provision of suitable host cells or one or more suitable secretion markers or mechanisms and/or transport systems for the host cells to secrete the protease into the fermentation medium. Without secretion, the protease can alternatively be isolated from the host cell, i.e. purified from the cell mass, for example by precipitation with ammonium sulphate or ethanol, or by chromatographic purification.

All of the above-mentioned aspects can be combined into methods in order to produce a protease.

An agent may include a protease as described above. The agent is preferably a washing or cleaning agent.

All conceivable types of washing or cleaning agents may be used, both concentrates and undiluted agents, for use on a commercial scale, in washing machines or for hand washing or cleaning. These include washing agents for textiles, carpets, or natural fibers, for which the term washing agent is used. These include, for example, dishwashing detergents for dishwashers or manual dishwashing detergents or cleaners for hard surfaces such as metal, glass, porcelain, ceramics, tiles, stone, painted surfaces, plastics, wood or leather, for which the term cleaning agent is used, i.e. in addition to manual and mechanical dishwashing detergents, also, for example, scouring agents, glass cleaners, WC toilet scenters, etc. The washing and cleaning agents also include auxiliary washing agents, which are added to the actual washing agent when washing textiles manually or using a machine in order to achieve an additional effect. Furthermore, washing and cleaning agents also include textile pre-treatment and post-treatment agents, i.e. those agents with which the item of laundry is brought into contact before the actual washing cycle, for example to loosen stubborn soilings, and also those agents which give the laundry further desirable properties such as a pleasant feel, crease resistance or low static charge in a step subsequent to the actual textile wash. Softeners are included, inter alia, in the last-mentioned agents.

The washing or cleaning agents, which may be in the form of powdered solids, in further-compacted particulate form, homogeneous solutions or suspensions, may contain, in addition to a protease, all known ingredients conventional in such agents, with preferably at least one further ingredient being present in the agent. The agents may in particular contain surfactants, builders, peroxygen compounds or bleach activators. They may also contain water-miscible organic solvents, further enzymes, sequestering agents, electrolytes, pH regulators and/or further auxiliaries such as optical brighteners, graying inhibitors, foam regulators, as well as dyes and fragrances, and combinations thereof.

In particular, a combination of a protease with one or more further ingredients of the agent is advantageous, since, in preferred embodiments, such an agent has improved cleaning performance by virtue of resulting synergisms. In particular, combining a protease with a surfactant and/or a builder and/or a peroxygen compound and/or a bleach activator can result in such a synergism. However, in preferred embodiments, the agent may not contain boric acid.

Advantageous ingredients of agents are disclosed in international patent application WO2009/121725, starting at the penultimate paragraph of page 5 and ending after the second paragraph on page 13. Reference is expressly made to this disclosure and the disclosure therein is incorporated in the present patent application by reference.

An agent advantageously contains the protease in an amount of from 2 µg to 20 mg, preferably from 5 µg to 17.5 mg, particularly preferably from 20 µg to 15 mg and very particularly preferably from 50 µg to 10 mg per g of the agent. In various embodiments, the concentration of the protease (active enzyme) described herein in the agent is >0 to 1 wt. %, preferably 0.001 to 0.1 wt. %, based on the total weight of the agent or composition. Furthermore, the protease contained in the agent, and/or other ingredients of the agent, may be coated with a substance which is impermeable to the enzyme at room temperature or in the absence of water, and which becomes permeable to the enzyme under conditions of use of the agent. Such an embodiment is thus characterized in that the protease is coated with a substance which is impermeable to the protease at room temperature or in the absence of water. Furthermore, the washing or cleaning agent itself can be packed in a container, preferably an air-permeable container, from which it is released shortly before use or during the washing process.

In further embodiments, the agent is characterized in that it (a) is present in solid form, in particular as a flowable powder having a bulk density of from 300 g/l to 1200 g/l, in particular from 500 g/l to 900 g/l, or
    (b) is present in pasty or liquid form, and/or
    (c) is present in gel form or in the form of dosing pouches, and/or
    (d) is present as a single-component system, or
    (e) is divided into a plurality of components.

These embodiments include all solid, powdered, liquid, gel or pasty administration forms of agents, which may optionally also consist of a plurality of phases and can be present in compressed or uncompressed form. The agent may be present as a flowable powder, in particular having a bulk density of from 300 g/l to 1200 g/l, in particular from 500 g/l to 900 g/l or from 600 g/l to 850 g/l. The solid administration forms of the agent also include extrudates, granules, tablets or pouches. Alternatively, the agent may also be in liquid, gel or pasty form, for example in the form of a non-aqueous liquid washing agent or a non-aqueous paste or in the form of an aqueous liquid washing agent or a water-containing paste. Liquid agents are generally preferred. The agent may also be present as a single-component system. Such agents consist of one phase. Alternatively, an agent may also consist of a plurality of phases. Such an agent is therefore divided into a plurality of components.

Washing or cleaning agents may contain only one protease. Alternatively, they may also contain other hydrolytic enzymes or other enzymes in a concentration that is expedient for the effectiveness of the agent. A further embodiment is therefore agents which further comprise one or more further enzymes. Further enzymes which can preferably be used are all enzymes which can exhibit catalytic activity in the agent, in particular a lipase, amylase, cellulase, hemi-cellulase, mannanase, tannase, xylanase, xanthanase, xyto-glucanase, ß-glucosidase, pectinase, carrageenase, perhy-drolase, oxidase, oxidoreductase or another protease, which is different from the proteases, as well as mixtures thereof. Further enzymes are advantageously contained in the agent in an amount of from $1 \times 10^{-8}$ to 5 wt. % in each case, based on active protein. Each further enzyme is contained in agents in an amount of, in order of increasing preference, from $1 \times 10^{-7}$ to 3 wt. %, from 0.00001 to 1 wt. %, from 0.00005 to 0.5 wt. %, from 0.0001 to 0.1 wt. %, and particularly preferably from 0.0001 to 0.05 wt. %, based on active protein. Particularly preferably, the enzymes exhibit syner-gistic cleaning performance on specific soilings or spots, i.e. the enzymes contained in the agent composition support one another in their cleaning performance. Very particularly preferably, there is such synergism between the protease contained and a further enzyme of an agent, including in particular between said protease and an amylase and/or a lipase and/or a mannanase and/or a cellulase and/or a pectinase. Synergistic effects can arise not only between different enzymes, but also between one or more enzymes and other ingredients of the agent.

In the cleaning agents described herein, the enzymes to be used may furthermore be formulated together with accom-panying substances, for example from fermentation. In liquid formulations, the enzymes are preferably used as enzyme liquid formulations.

The enzymes are generally not provided in the form of pure protein, but rather in the form of stabilized, storable and transportable preparations. These pre-formulated prepara-tions include, for example, the solid preparations obtained through granulation, extrusion, or lyophilization or, in par-ticular in the case of liquid or gel agents, solutions of the enzymes, advantageously maximally concentrated, low-wa-ter, and/or supplemented with stabilizers or other auxiliaries.

Alternatively, the enzymes can also be encapsulated, for both the solid and the liquid administration form, for example by spray-drying or extrusion of the enzyme solu-tion together with a preferably natural polymer or in the form of capsules, for example those in which the enzymes are enclosed in a set gel, or in those of the core-shell type, in which an enzyme-containing core is coated with a water-, air-, and/or chemical-impermeable protective layer. Further active ingredients such as stabilizers, emulsifiers, pigments, bleaching agents, or dyes can additionally be applied in overlaid layers. Such capsules are applied using inherently known methods, for example by shaking or roll granulation or in fluidized bed processes. Such granules are advanta-geously low in dust, for example due to the application of polymeric film-formers, and stable in storage due to the coating.

Moreover, it is possible to formulate two or more enzymes together, such that a single granule has a plurality of enzyme activities.

The enzymes can also be introduced into water-soluble films, such as those used in the formulation of washing and cleaning agents in a unit dosage form. Such a film allows the release of the enzymes following contact with water. As used herein, "water-soluble" refers to a film structure that is preferably completely water-soluble. Preferably, such a film consists of (fully or partially hydrolyzed) polyvinyl alcohol (PVA).

A method for cleaning textiles or hard surfaces, which is characterized in that an agent may be used in at least one method step, or in that a protease becomes catalytically active in at least one method step, in particular such that the protease is used in an amount of from 40 µg to 4 g, preferably from 50 µg to 3 g, particularly preferably from 100 µg to 2 g, and very particularly preferably from 200 µg to 1 g, or in the concentrations described herein.

In various embodiments, the method described above is characterized in that the protease is used at a temperature of 0-100° C., preferably 0-60° C., more preferably 20-40° C. and most preferably at a temperature of 25° C.

These include both manual and mechanical methods, with mechanical methods being preferred. Methods for cleaning textiles are generally characterized in that, in a plurality of method steps, various cleaning-active substances are applied to the material to be cleaned and are washed off after the exposure time, or in that the material to be cleaned is otherwise treated with a washing agent or a solution or dilution of this agent. The same applies to methods for cleaning all materials other than textiles, in particular hard surfaces. All conceivable washing or cleaning methods can be enhanced in at least one of the method steps by the use of a washing or cleaning agent or a protease, and then constitute non-limiting embodiments. All aspects, objects and embodiments described for the protease and agents containing it are also usable herein. Therefore, reference is expressly made at this point to the disclosure at the appro-priate point with the note that this disclosure also applies to the above-described methods.

Since proteases naturally already have hydrolytic activity and also exhibit this in media which otherwise have no cleaning power, for example in a simple buffer, a single and/or the sole step of such a method can consist in a protease, which is the only cleaning-active component, being brought into contact with the soiling, preferably in a buffer solution or in water. This constitutes a further embodi-ment usable herein.

Alternative embodiments are also represented by methods for treating textile raw materials or for textile care, in which a protease becomes active in at least one method step. Among these, methods for textile raw materials, fibers or textiles with natural constituents are preferred, and very particularly for those with wool or silk.

Finally, the proteases described herein may be used in washing or cleaning agents, for example as described above, for the (improved) removal of protein-containing soilings, for example from textiles or hard surfaces. In preferred embodiments of this use, the protease in the washing or cleaning agent is stored for 3 or more days, 4 or more days, 7 or more days, 10 or more days, 12 or more days, 14 or more days, 21 or more days or 28 or more days before a washing or cleaning process.

All aspects, objects and embodiments described for pro-teases and agents containing them are also usable herein. Therefore, reference is expressly made at this point to the disclosure at the appropriate point with the note that this disclosure also applies to the above-described use.

EXAMPLES

Overview of the Mutations:

From a subtilisin-type alkaline protease from *Bacillus pumilus* (wild-type *Bacillus pumilus* protease DSM18097 according to SEQ ID NO:1), variants were produced by random mutagenesis, which were then screened, inter alia for improved wash performance and/or enzyme stability. In this way, a performance-enhanced mutant (mutant 1) was generated from the above-mentioned protease (SEQ ID NO: 1). The mutants 2-10 build on this mutant.

| Variant | Amino acid substitutions relative to SEQ ID NO: 1 | | | | | | |
|---|---|---|---|---|---|---|---|
| Mutant 1 | P9T | N130D | Q271E | N144K | N252T | T133A | |
| Mutant 2 | P9T | N130D | Q271E | N144K | N252T | T133A | T218S |
| Mutant 3 | P9T | N130D | Q271E | N144K | N252T | T133A | L82F |
| Mutant 4 | P9T | N130D | Q271E | N144K | N252T | T133A | S156D | T162I |
| Mutant 5 | P9T | N130D | Q271E | N144K | N252T | T133A | T3K | V4I |
| Mutant 6 | P9T | N130D | Q271E | N144K | N252T | T133A | T3A | V4A |
| Mutant 7 | P9T | N130D | Q271E | N144K | N252T | T133A | T3A | V4I |
| Mutant 8 | P9T | N130D | Q271E | N144K | N252T | T133A | T3R | |
| Mutant 9 | P9T | N130D | Q271E | N144K | N252T | T133A | | V4A |
| Mutant 10 | P9T | N130D | Q271E | N144K | N252T | T133A | T3S | V4T |

Washing Agent Matrix Used

The following washing agent matrix (commercially available, without enzymes, opt. brighteners, perfume and dyes) is the matrix that was used for the test:

| Chemical name | Wt. % of active substance in the raw material | Wt.% of active substance in the formulation |
|---|---|---|
| Demineralized water | 100.0 | Remainder |
| Protease stabilizer | 100.0 | 0.5-1.5 |
| Citric acid | 100.0 | 3-5 |
| Defoamer | 100.0 | <1 |
| FAEOS | 70.0 | 4-8 |
| FAEO, non-ionic surfactant | 100.0 | 8-14 |
| LAS | 96.0 | 12-18 |
| Palm kernel oil fatty acid | 30.0 | 2-4 |
| MEA | 100.0 | 4-8 |
| NaOH | 50.0 | 0.5-2 |
| Glycerol | 99.5 | 1-3 |
| Propanediol-1,2 | 100.0 | 8-12 |
| HEDP | 60.0 | 0.5-2 |
| SRP (soil release polymer) | 30.0 | 0.5-1 |

Without opt. brighteners, perfume and enzymes; dosage 3.17 g/l

Protease Activity Assays

The activity of the protease is determined by the release of the chromophore para-nitroaniline from the substrate succinyl alanine-alanine-proline-phenylalanine-para-nitroanilide (AAPFpNA; Bachem L-1400). The release of the pNA causes an increase in absorbance at 410 nm, the temporal progression of which is a measure of the enzymatic activity.

The measurement was carried out at a temperature of 25° C., a pH of 8.6, and a wavelength of 410 nm. The measuring time was 5 minutes with a measuring interval of from 20 to 60 seconds.

Measurement Approach:

10 µL AAPF solution (70 mg/mL)

1000 µL Tris/HCl (0.1 M, pH 8.6 with 0.1% Brij 35)

10 µL diluted protease solution

Kinetics created over 5 min at 25° C. (410 nm)

Mini Washing Test and Results

Washing test with *Bacillus subtilis* culture supernatants which contain the screened protease mutants by heterologous expression. The supernatants are used in washing agents in the equivalent activity to the reference protein (according to SEQ ID NO:1) at a market-standard concentration for proteases. The mutants are all based on the wash performance of the starting variant (mutant 1), which is set equal to 100% (sum of the 6 soilings, corrected by the performance of the washing agent alone).

Conditions: 40° C., 16° dH water, 1 h

Soilings:

1. CFT CS038

2. CFT PC-10

3. WfK 10N

4. CFT C-03

5. CFT C-05

6. H-MR-B

Punched-out pieces of fabric (diameter=10 mm) were placed in microtiter plates, washing liquor was preheated to 40° C., with a final concentration of 3.17 g/l, the liquor and enzyme were added to the soiling and incubated for 1 h at 40° C. and 600 rpm, then the soiling was rinsed several times with clear water and left to dry and the brightness was determined using a color-measuring device. The lighter the fabric, the better the cleaning performance. The L value=brightness is measured here, and the higher the brighter. The sum of the 6 soilings is given in % based on the starting variant (mutant 1), corrected by the performance of the washing agent without protease.

| Variant | Performance in washing test at 40° C. (based on the performance of mutant 1) |
|---|---|
| Mutant 1 | 100% |
| Mutant 2 | 117% |
| Mutant 3 | 123% |
| Mutant 4 | 106% |
| Mutant 5 | 150% |
| Mutant 6 | 126% |
| Mutant 7 | 118% |
| Mutant 8 | 118% |
| Mutant 9 | 107% |
| Mutant 10 | 107% |

All variants show an increased wash performance in comparison with the starting mutant 1.

Furthermore, all variants show an increased wash performance in comparison with the starting variant (mutant 1).

The invention claimed is:

1. A composition, comprising:

a protease with a conservatively mutated amino acid sequence having at least 95% sequence identity with the amino acid sequence of SEQ ID NO:1 over its entire length, in each case based on the numbering according to SEQ ID NO:1, wherein the protease comprises:

(i) amino acid substitutions at the positions corresponding to positions 9, 133, 144, 252, and 271; wherein, the substitutions at positions 133 and 252 are 133A and 252T; and, (ii) at least one further amino acid substitution at at least one of the positions corresponding to positions 3, 4, 82, 156, 162, 218, and combinations thereof; and, wherein the protease exhibits improved cleaning performance when compared to the protease of SEQ ID NO:1.

2. The protease according to claim 1, wherein the protease further has an additional amino acid substitution at the position corresponding to position 130.

3. The protease according to claim 1, wherein:

a) the amino acid substitution at the position corresponding to position 3 is selected from the group consisting of 3K, 3A, 3R, and 3S;

b) the amino acid substitution at the position corresponding to position 4 is selected from the group consisting of 4A, 4I, and 4T;

c) the amino acid substitution at the position corresponding to position 82 is 82F;

d) the amino acid substitution at the position corresponding to position 156 is 156D;

e) the amino acid substitution at the position corresponding to position 162 is 162I;

f) the amino acid substitution at the position corresponding to position 218 is 218S; and g) combinations thereof.

4. The protease according to claim 1, wherein the amino acid substitution at the position corresponding to position 3 is 3K, and the amino acid substitution at the position corresponding to position 4 is 4I.

5. The protease according to claim 1, further comprising:

single or multiple conservative amino acid substitution, fragmentation, deletion, insertion, substitution mutagenesis, and combinations thereof.

6. A nucleic acid that codes for a protease according to claim 1.

7. A vector comprising a nucleic acid according to claim 6.

8. A non-human host cell comprising a protease according to claim 1.

9. A method for producing a protease variant, wherein the method comprises:

a) cultivating a host cell according to claim 8; and b) isolating the protease variant from the culture medium or from the host cell.

10. An agent comprising the protease according to claim 1.

11. A method for cleaning textiles or hard surfaces, wherein the method comprises:

applying the agent of claim 10 to a textile, hard surface, or combinations thereof.

* * * * *

SEQUENCE LISTING

<160> NUMBER OF SEQ ID NOS: 1

<210> SEQ ID NO 1
<211> LENGTH: 275
<212> TYPE: PRT
<213> ORGANISM: Bacillus pumilus

<400> SEQUENCE: 1

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
                20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
        50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
            115                 120                 125

Pro Asn Gly Ser Thr Ala Leu Lys Asn Ala Val Asp Thr Ala Asn Asn
        130                 135                 140

Arg Gly Val Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
        210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Ala Gln Ala
            260                 265                 270

Ala Ser Asn
        275